US008932866B2

(12) United States Patent
Natsugoe et al.

(10) Patent No.: US 8,932,866 B2
(45) Date of Patent: Jan. 13, 2015

(54) METHOD FOR INSPECTING GASTROENTEROLOGICAL CANCER BY UTILIZING N-LINKED SUGAR CHAIN

(75) Inventors: Shoji Natsugoe, Kagoshima (JP); Yasuto Uchikado, Kagoshima (JP); Teruto Hashiguchi, Kagoshima (JP); Hiroyuki Shinchi, Kagoshima (JP); Kosei Maemura, Kagoshima (JP); Yuko Mataki, Kagoshima (JP); Norichika Moriwaki, Tokyo (JP); Masaru Sekijima, Tokyo (JP); Hideyuki Shimaoka, Tokyo (JP); Midori Abe, Tokyo (JP); Masao Fukushima, Tokyo (JP); Kota Igarashi, Tokyo (JP); Hiroki Abe, Tokyo (JP); Taichi Aihara, Tokyo (JP)

(73) Assignees: Kagoshima University, Kagoshima-shi (JP); Sumitomo Bakelite Co., Ltd., Tokyo (JP)

( * ) Notice: Subject to any disclaimer, the term of this patent is extended or adjusted under 35 U.S.C. 154(b) by 0 days.

(21) Appl. No.: 13/639,724

(22) PCT Filed: Apr. 6, 2011

(86) PCT No.: PCT/JP2011/058727
§ 371 (c)(1),
(2), (4) Date: Dec. 18, 2012

(87) PCT Pub. No.: WO2011/126053
PCT Pub. Date: Oct. 13, 2011

(65) Prior Publication Data
US 2013/0109043 A1 May 2, 2013

(30) Foreign Application Priority Data

Apr. 6, 2010 (JP) .................................. 2010-088089

(51) Int. Cl.
G01N 33/66 (2006.01)
G01N 33/48 (2006.01)
C12Q 1/54 (2006.01)
C12Q 1/00 (2006.01)
G01N 33/50 (2006.01)
G01N 33/574 (2006.01)

(52) U.S. Cl.
CPC .......... *G01N 33/50* (2013.01); *G01N 33/57446* (2013.01); *G01N 33/66* (2013.01)
USPC ................. 436/94; 436/93; 436/91

(58) Field of Classification Search
CPC ....... G01N 33/66; G01N 33/00; G01N 33/50; G01N 33/48; C12Q 1/006; C12Q 1/54; C12Q 1/00
USPC .............................. 436/94, 93, 91
See application file for complete search history.

(56) References Cited

U.S. PATENT DOCUMENTS

| 5,998,165 | A | 12/1999 | Goold et al. |
| 7,947,504 | B2 | 5/2011 | Miyoshi et al. |
| 8,372,647 | B2 * | 2/2013 | Arao et al. ...................... 436/64 |

FOREIGN PATENT DOCUMENTS

| JP | 2000 502902 | 3/2000 |
| JP | 2001 33460 | 2/2001 |
| JP | 2002 112799 | 4/2002 |
| JP | 2003 532389 | 11/2003 |
| JP | 2004 248575 | 9/2004 |
| JP | 2009 168470 | 7/2009 |
| WO | WO 2009/136506 | * 11/2009 ........... G01N 33/574 |

OTHER PUBLICATIONS

Zhao et al., N-linked Glycosylation Profiling of Pancreatic Cancer Serum Using Capillary Liquid Phase Separation Coupled with Mass Spectrometric Analysis, Journal of Proteome Research, 2007, vol. 6, No. 3, p. 1126-1138.*
Zhao, J., et al., "N-linked Glycosylation Profiling of Pancreatic Cancer Serum Using Capillary Liquid Phase Separation Coupled with Mass Spectrometric Analysis," Journal of Proteome Research, vol. 6, pp. 1126-1138, (2007).
Nakano, M., et al., "Site-specific analysis of N-glycans on haptoglobin in sera of patients with pancreatic cancer: A novel approach for the development of tumor markers," International Journal of Cancer, vol. 122, pp. 2301-2309, (2008).
International Search Report Issued May 24, 2011 in PCT/JP11/58727 Filed Apr. 6, 2011.
Zhao, J., et al., "Glycoprotein Microarrays with Multi-Lectin Detection: Unique Lectin Binding Patterns as a Tool for Classifying Normal, Chronic Pancreatitis and Pancreatic Cancer Sera," Journal of Proteome Research, vol. 6, pp. 1864-1874, (2007).
Koprowski, H., et al., "Colorectal Carcinoma Antigens Detected by Hybridoma Antibodies," Somatic Cell Genetics, vol. 5, No. 6, pp. 957-972, (1979).
Metzgar, R.S., et al., "Antigens of Human Pancreatic Adenocarcinoma Cells Defined by Murine Monoclonal Antibodies," Cancer Research, vol. 42, pp. 601-608, (Feb. 1982).
Lindholm, L., et al., "Monoclonal Antibodies against Gastrointestinal Tumor-Associated Antigens Isolated as Monosialogangliosides," Int. Archs Allergy appl. Immun., vol. 71, pp. 178-181, (1983).
"Monoclonal Antibody Span-1 Against Pancreatic Cancer cell and Characterization of Antigen," Journal of Japan Surgical Society, vol. 87, No. 2, pp. 236-240, (1986) (with English translation).
U.S. Appl. No. 14/349,855, filed Apr. 4, 2014, Natsugoe, et al.

* cited by examiner

Primary Examiner — Christine T Mui
(74) Attorney, Agent, or Firm — Oblon, Spivak, McClelland, Maier & Neustadt, L.L.P.

(57) ABSTRACT

As a result of collecting blood from pancreatic cancer patients, esophageal cancer patients, and stomach cancer patients, and conducting mass spectrometry on N-linked sugar chains in the plasmas, sugar chains whose abundances are significantly different from those of healthy subjects have been successfully identified from the blood samples of the cancer patients.

20 Claims, 4 Drawing Sheets

METHOD FOR INSPECTING GASTROENTEROLOGICAL CANCER BY UTILIZING N-LINKED SUGAR CHAIN

TECHNICAL FIELD

The present invention relates to a method for inspecting a gastroenterological cancer by utilizing an N-linked sugar chain as a diagnostic marker for the gastroenterological cancer.

BACKGROUND ART

The gastroenterological tract refers to organs playing roles of food ingestion, transport, digestion, absorption of nutrients, and excretion. In the gastroenterological tract, the pancreas is an organ approximately 15 cm long and located behind the stomach. The major diseases are pancreatic cancer and pancreatitis. Particularly, pancreatic cancer is known as one of cancers whose mortality rate among Japanese is increasing. The cause of the pancreatic cancer has not been revealed completely, but the risk factors are presumably excessive intakes of animal fats, proteins, alcohols, and so forth due to Westernization of dietary habits, or smoking and others. In addition, those who have a medical history of chronic pancreatitis, pancreatolithiasis, diabetes, or acute pancreatitis are also thought be in a high risk group of pancreatic cancer. Pancreatic cancer is a cancer developed from a cell having an exocrine function, particularly a cell of the pancreatic duct through which pancreatic juices flow. This type of cancer accounts for 90% or more of pancreatic cancer. Pancreatic cancer has very high malignancy, and metastasizes to another organ at an early stage. Accordingly, early detection is one of the challenges. However, the pancreas exists in the retroperitoneal space and is surrounded by many organs such as the stomach, duodenum, spleen, small intestine, large intestine, liver, and gallbladder. For this reason, it is quite difficult to detect a cancer at the initial stage even by using various kinds of image diagnoses. At present, the cancer is often detected in an advanced state.

Stomach cancer occurs frequently in Japan and Southeast Asia. In the world, the mortality rate of stomach cancer is the second highest among cancers. The prognosis of stomach cancer has been improved by the advancement of diagnostic techniques and treatment methods, but it cannot be said that the prognosis of advanced stomach cancer is favorable yet. As the indicator of the prognosis of stomach cancer having invaded stomach serosa, the five-year survival rate is as low as 35%. One of the main causes of the recurrence after curative resection of advanced cancer is peritoneal metastasis. The therapeutic effects on peritoneal metastasis recurrence by the advancement of chemotherapy have also been observed, but the five-year survival rate is still low. Many steps and many genes are known to be involved in the mechanism of the peritoneal metastasis of stomach cancer. It has been reported that an adhesion molecule-related gene, an apoptosis-related gene, and other genes are deeply involved in the peritoneal metastasis of stomach cancer. Further researches are necessary to reveal the mechanisms of the metastasis of stomach cancer including the peritoneal metastasis of stomach cancer.

Esophageal cancer develops in middle thoracic esophagus in approximately half of cases. In Japan, squamous epithelial cancer accounts for 90% or more of esophageal cancer. Both of the morbidity rate and the mortality rate of men are 5 times or more higher than those of women. It has been previously reported that drinking alcohol and smoking are involved in the carcinogenesis of esophageal cancer. Recently, the involvement of ALDH2 has been reported. A surgery on esophageal cancer is a highly invasive procedure, and esophageal cancer is a disease with an unfavorable prognosis. Recently, with increased incidences of early-stage cancer, there is also increased the number of cases that can be cured completely by an endoscopic therapy. Furthermore, chemoradiotherapy has also demonstrated the effects, and the improvement in therapeutic outcome has been observed. Nevertheless, the prognosis of unresectable advanced cancers is still unfavorable. It is desired to establish a new screening system for early-stage cancer detection and make an advancement of chemotherapy in the future.

One of the cancer-detecting and diagnosing methods having been developed so far is measurement of a tumor marker. Blood tumor markers for diagnosing pancreatic cancer have been already developed such for example as CA19-9 (NPL 1), Dupan-2 (NPL 2), CA-50 (NPL 3), and Span-1 (NPL 4). In addition, several patent publications disclose methods for detecting and diagnosing pancreatic cancer by using a marker of a gene specifically expressed in a tumor cell. Up to now, PANCIA and PANCIB (PTL 1) as well as KCCR13L (PTL 2) have been disclosed as marker genes for pancreatic cancer. Moreover, since a DNA is amplified or deleted at a specific site of a chromosome of pancreatic cancer cells, there is also proposed a method for diagnosing pancreatic cancer by detecting an amplification or deletion at a chromosome site specific to pancreatic cancer.

Further, tumor marker measurement for stomach cancer is characterized by using as a marker a variation in an amount of an already-known non-triple-helical C-terminal telopeptide of type I collagen (ICTP) expressed. There are proposed an appropriate diagnosing marker for advanced stomach cancer, particularly scirrhus stomach cancer (see PTL 3), and a method including: counting the number of demethylated DNAs present in a repeated DNA sequence obtained from a cancerous or non-cancerous tissue specimen; and judging, based on the percentage of demethylated DNAs, whether a prognosis of various cancer diseases such as stomach cancer is favorable or not (see for example, PTL 4).

Further, as to metastatic colorectal cancer, or primary/metastatic stomach cancer or esophageal cancer, there is proposed a screening method using an expression of SI, CDX1, or CDX2 as an index (see PTL 5).

However, a tumor marker is used to grasp the kinetics of an advanced malignant tumor at present. No method for detecting and diagnosing a cancer by utilizing a tumor marker, which is adoptable for early diagnosis has been established yet. Particularly, it is difficult to diagnose pancreatic cancer at an early stage, and the therapeutic outcome is not favorable. A met hod applicable to screening has to be developed as soon as possible.

CITATION LIST

Patent Literatures

[PTL 1] International Application Japanese-Phase Publication No. 2000-502902
[PTL 2] Japanese Patent Application No. 2003-041843
[PTL 3] Japanese Unexamined Patent Application Publication No. 2001-33460
[PTL 4] Japanese Unexamined Patent Application Publication No. 2002-112799
[PTL 5] International Application Japanese-Phase Publication No. 2003-532389

Non Patent Literatures

[NPL 1] Somatic Cell Genet., 5, 957-972, 1979
[NPL 2] Cancer Res., 42, 601, 1982

[NPL 3] Int. Arch. Allergy Appl. Immunol., 71, 178-181, 1983
[NPL 4] Journal of Japan Surgical Society, 87, 236, 1986

[Summary of Invention]

Technical Problem

The present invention has been made in consideration of such circumstances. An object of the present invention is to provide a method capable of easily inspecting a gastroenterological cancer at an early stage.

Solution to Problem

In order to achieve the above-described object, the present inventors have focused on sugar chains of a glycoprotein contained in a blood sample of a gastroenterological cancer patient and attempted to develop a novel method for inspecting a gastroenterological cancer. Specifically, blood was collected from 17 pancreatic cancer patients, 34 esophageal cancer patients, and 22 stomach cancer patients. Then, mass spectrometry was conducted on N-linked sugar chains in the plasmas. As a result, sugar chains whose abundances were significantly different from those of healthy subjects were successfully identified from the blood samples of the cancer patients. This has led to the completion of the present invention.

In other words, the present invention relates to a method for inspecting a gastroenterological cancer by detecting a specific N-linked sugar chain in blood collected from a subject. More specifically, the present invention provides the following inventions.

[1] A method for inspecting a gastroenterological cancer, comprising the steps of:
(a) releasing sugar chains from a glycoprotein in blood collected from a subject;
(b) purifying the released sugar chains; and
(c) detecting a sugar chain showing properties (i) and (ii) below in the purified sugar chains:
(i) the sugar chain being an N-linked sugar chain, and
(ii) when mass spectrometry is conducted with a MALDI-TOF-MS analyzer, the sugar chain showing a peak at a mass-to-charge ratio (m/z) of anyone of 2521, 2216, 2054, 2681, 3108, 2695, 1326, 1892, 2172, 2257, 2334, 2375, 2639, 2703, 2725, 2827, and 3030.

[2] A method for inspecting a gastroenterological cancer, comprising the steps of:
(a) releasing sugar chains from a glycoprotein in blood collected from a subject;
(b) purifying the released sugar chains; and
(c) detecting at least any one of the following sugar chains in the purified sugar chains:

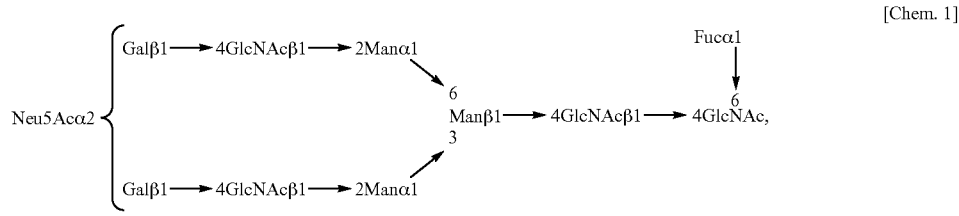

[Chem. 1]

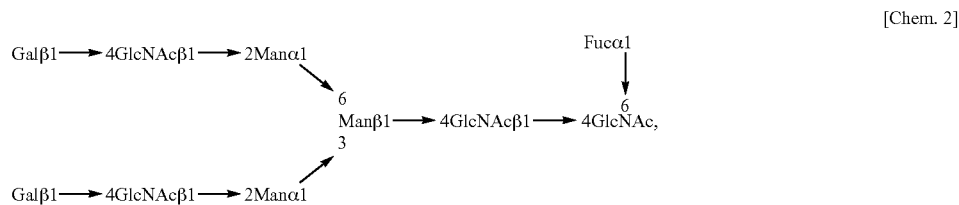

[Chem. 2]

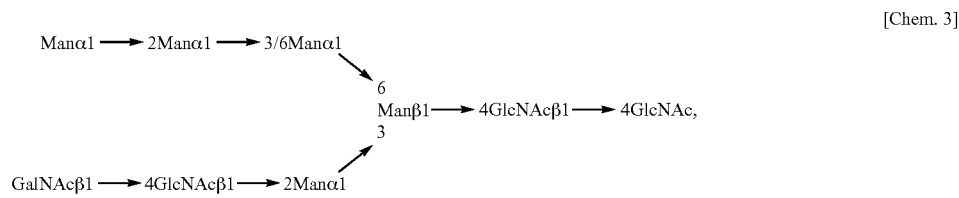

[Chem. 3]

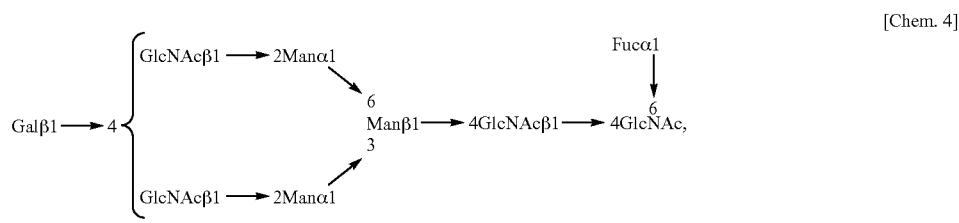

[Chem. 4]

[Chem. 5]

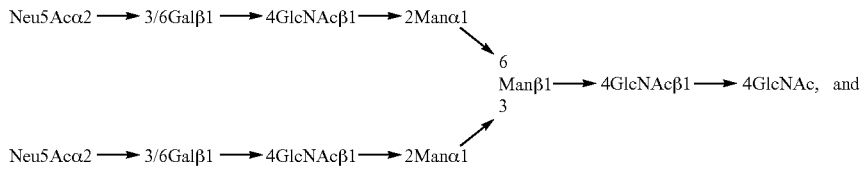

[Chem. 6]

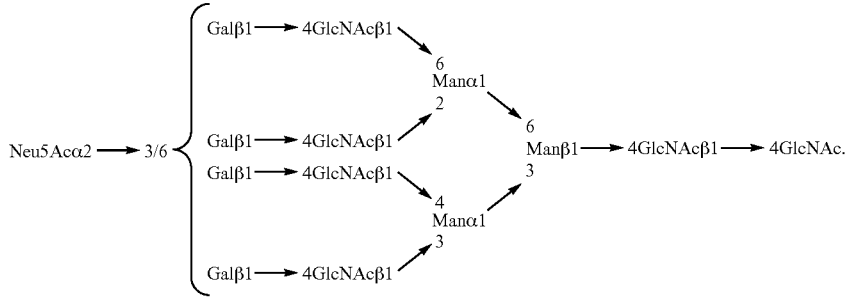

[3] The method according to any one of [1] and [2], wherein the gastroenterological cancer is any one of pancreatic cancer, esophageal cancer, and stomach cancer.

Advantageous Effect of Invention

The present invention makes it possible to easily inspect a gastroenterological cancer at an early stage of the cancer by detecting a specific N-linked sugar chain in blood collected from a subject.

DESCRIPTION OF EMBODIMENTS

Figure 1:
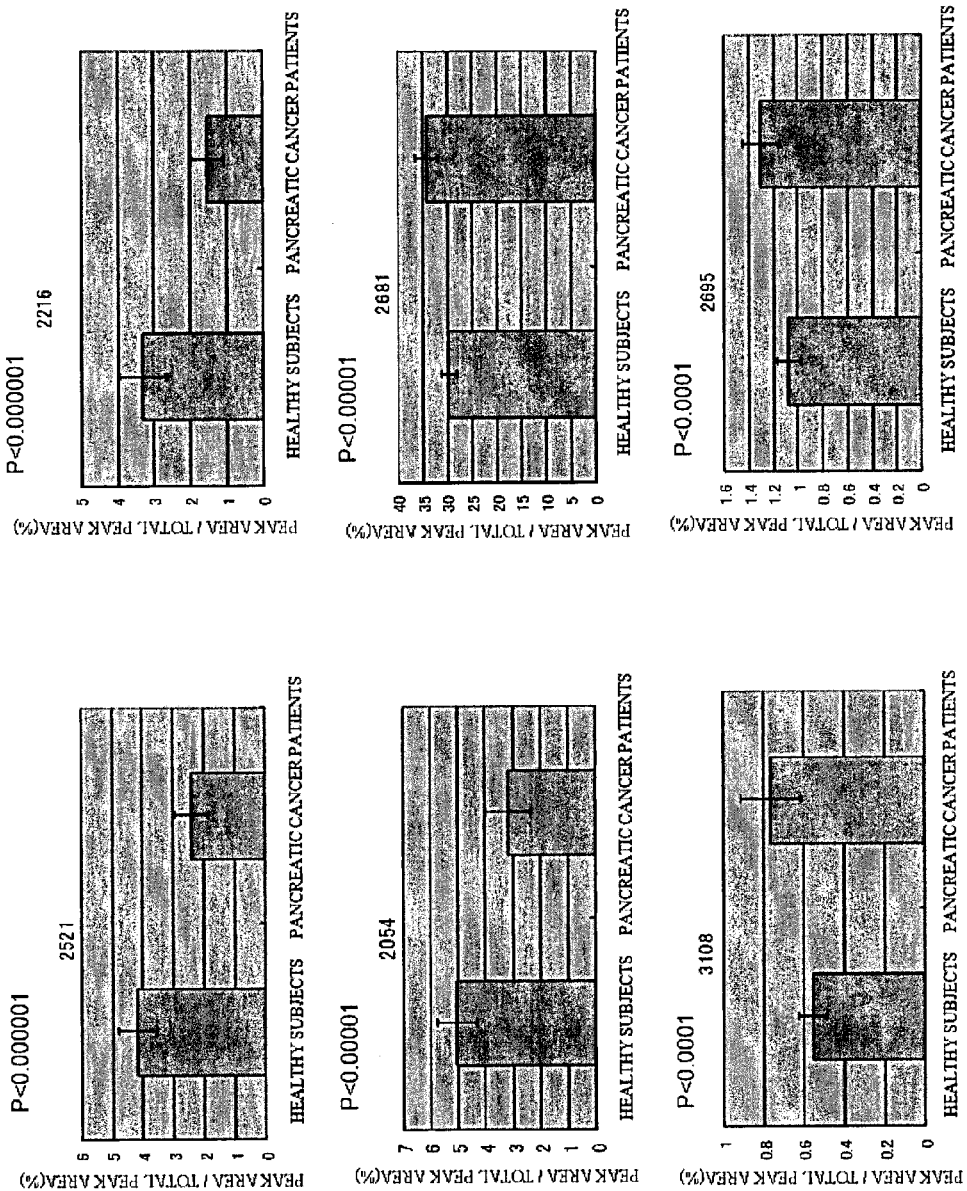
FIG. 1 shows graphs illustrating the result of quantifying the abundance of sugar chains in each specimen, the sugar chains having been determined to be significantly different by a T-test conducted between two groups of a healthy subject group and a pancreatic cancer group. A total signal amount indicating the abundance of the sugar chains was calculated, and corrected by the percentages of the sugar chains in the specimen.

The present invention provides a method for inspecting a gastroenterological cancer, comprising the steps of:
releasing sugar chains from a glycoprotein in blood collected from a subject (step (a));
purifying the released sugar chains (step (b)); and
detecting a sugar chain showing properties (i) and (ii) below in the purified sugar chains (step (c)):
(i) the sugar chain being an N-linked sugar chain, and
(ii) when mass spectrometry is conducted with a MALDI-TOF-MS analyzer, the sugar chain showing a peak at amass-to-charge ratio (m/z) of any one of 2521, 2216, 2054, 2681, 3108, 2695, 1326, 1892, 2172, 2257, 2334, 2375, 2639, 2703, 2725, 2827, and 3030.

The "gastroenterological cancer" for which the inspection method of the present invention is employed is not particularly limited. The present invention is particularly useful for pancreatic cancer and esophageal cancer, which are refractory cancers, as well as stomach cancer, which occurs frequently.

The "blood collected from a subject" is a sample in the method for inspecting a gastroenterological cancer of the present invention, and may be whole blood including all of the blood components, or a serum, a plasma, or the like separated from the blood. A serum or a plasma is preferable, and, a plasma is particularly preferable.

In the present invention, the method for releasing the sugar chains from the glycoprotein in the blood is not particularly limited. Examples thereof include enzymatic methods using N-glycosidase F (also called glycopeptidase, PN Gase, glycanase, glycoamidase, and so on), glycopeptidase A, or the like, and a hydrazine decomposition method. Above all, an enzymatic method with N-glycosidase F can be suitably used. In this case, a protease such as trypsin can be used in combination.

In the present invention, the method for purifying the released sugar chains is particularly not limited, as long as the sugar chains from a mixture in the sample are selectively captured and purified by the method. Particularly suitable is a method using BlotGlyco (registered trademark) (manufactured by Sumitomo Bakelite Co., Ltd.), which is sugar chain-capturing beads optimized for high sensitivity measurement by MALDI-TOF-MS and high-performance liquid chromatography (HPLC).

In the present invention, a sugar chain is detected in the purified sugar chains. The sugar chain is an N-linked sugar chain. When the mass spectrometry is conducted with the MALDI-TOF-MS analyzer, the sugar chain shows a peak at a mass-to-charge ratio (m/z) of any one of 2521, 2216, 2054, 2681, 3108, 2695, 1326, 1892, 2172, 2257, 2334, 2375, 2639, 2703, 2725, 2827, and 3030. In the present invention, it is particularly preferable to detect a sugar chain showing a peak at a mass-to-charge ratio (m/z) of any one of 2521 and 2216. It should be noted that a measurement error of within ±1 may arise in the aforementioned values of the mass-to-charge ratio (m/z).

chain or asparagine-linked sugar chain. In addition, "MALDI-TOF-MS" is a method for measuring the mass on the basis of the time of flight by utilizing MALDI. MALDI is method including: spotting a sample on a plate; then adding a matrix solution (2,5-Dihydroxybenzoic acid) thereto, followed by solidification by drying to a crystalline state; and applying a high energy onto the matrix by pulsed laser irradiation to desorb sample-derived and matrix-derived ions such as $(M+H)^+$ and $(M+Na)^+$. When an ion is accelerated at a constant accelerating voltage V, the mass-to-charge ratio (m/z) of an ion can be expressed as "$m/z=2\,eVt^2/L^2$," where m is the mass of the ion, v is the velocity of the ion, z is the charge number of the ion, e is the elementary charge, and t is the time of flight of the ion.

In the present invention, the sugar chain having a peak at the mass-to-charge ratio (m/z) of 2521 in the mass spectrometry conducted using the MALDI-TOF-MS analyzer is a sugar chain showing a mass spectral peak at m/z of 2521 as a result of the mass spectrometry with the MALDI-TOF-MS analyzer. The structural formula is estimated to be:

[Chem. 7]

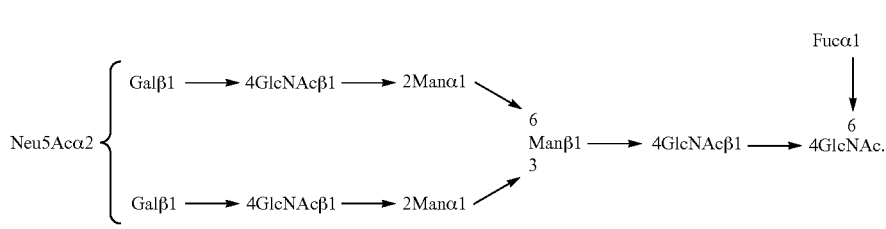

Moreover, in the present invention, the sugar chain having a peak at the mass-to-charge ratio (m/z) of 2216 in the mass spectrometry conducted using the MALDI-TOF-MS analyzer is a sugar chain showing a mass spectral peak at m/z of 2216 as a result of the mass spectrometry with the MALDI-TOF-MS analyzer. The structural formula is estimated to be:

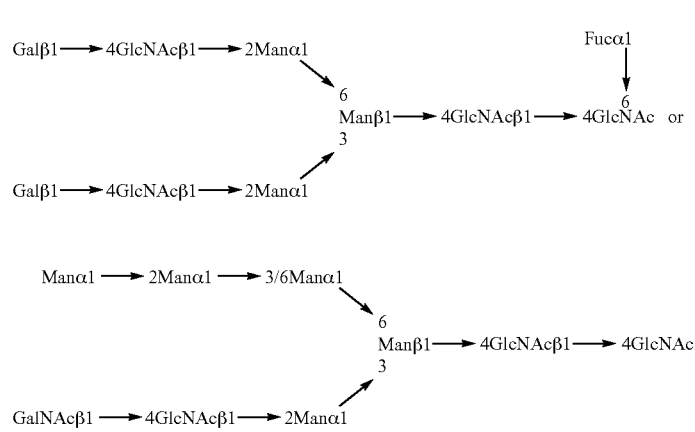

Herein, the "N-linked sugar chain" is a sugar chain of a glycoprotein and attached to a nitrogen atom of an amide group at a side chain of an asparagine residue of the protein. The "N-linked sugar chain" is also called an N-type sugar Moreover, in the present invention, the sugar chain having a peak at the mass-to-charge ratio (m/z) of 2054 in the mass spectrometry conducted using the MALDI-TOF-MS analyzer is a sugar chain showing a mass spectral peak at m/z of 2054 as a result of the mass spectrometry with the MALDI-TOF-MS analyzer. The structural formula is estimated to be:

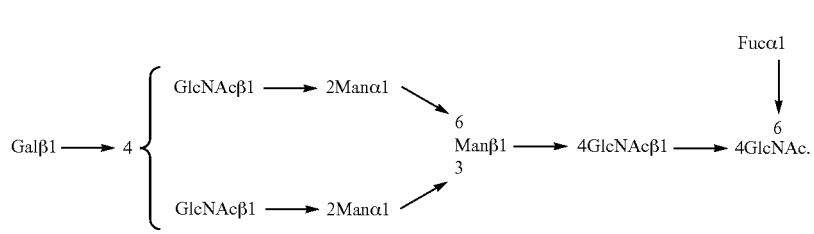
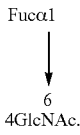

Moreover, in the present invention, the sugar chain having a peak at the mass-to-charge ratio (m/z) of 2681 in the mass spectrometry conducted using the MALDI-TOF-MS analyzer is a sugar chain showing a mass spectral peak at m/z of 2681 as a result of the mass spectrometry with the MALDI-TOF-MS analyzer. The structural formula is estimated to be:

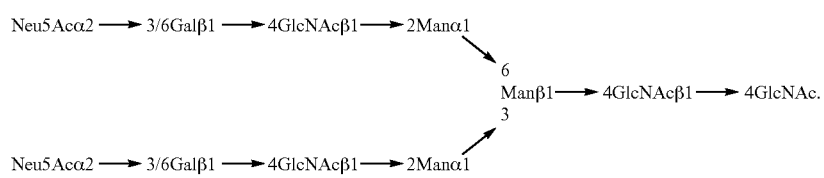

Moreover, in the present invention, the sugar chain having a peak at the mass-to-charge ratio (m/z) of 3108 in the mass spectrometry conducted using the MALDI-TOF-MS analyzer is a sugar chain showing a mass spectral peak at m/z of 3108 as a result of the mass spectrometry with the MALDI-TOF-MS analyzer. The structural formula is estimated to be:

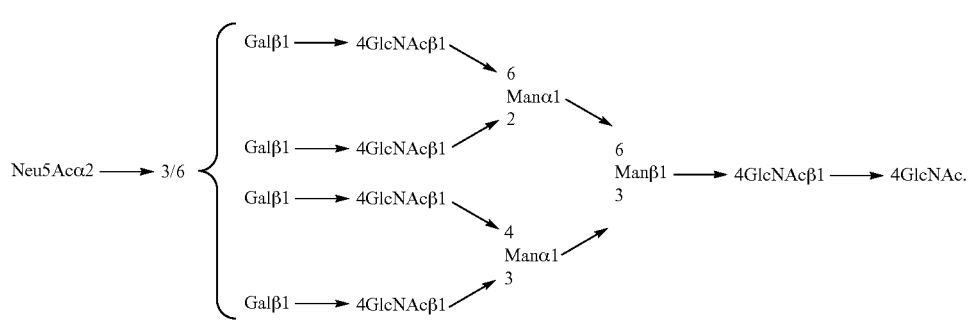

Moreover, in the present invention, the sugar chain having a peak at the mass-to-charge ratio (m/z) of 1326 in the mass spectrometry conducted using the MALDI-TOF-MS analyzer is a sugar chain showing a mass spectral peak at m/z of 1326 as a result of the mass spectrometry with the MALDI-TOF-MS analyzer. The structural formula is estimated to be: $(Hex)_2(HexNAc)_2(Deoxyhexose)_1$ (Table 1).

Moreover, in the present invention, the sugar chain having a peak at the mass-to-charge ratio (m/z) of 1892 in the mass spectrometry conducted using the MALDI-TOF-MS analyzer is a sugar chain showing a mass spectral peak at m/z of 1892 as a result of the mass spectrometry with the MALDI-TOF-MS analyzer. The structural formula is estimated to be: $(HexNAc)_2(Deoxyhexose)_1+(Man)_3(GlcNAc)_2$ (Table 1).

Moreover, in the present invention, the sugar chain having a peak at the mass-to-charge ratio (m/z) of 2172 in the mass spectrometry conducted using the MALDI-TOF-MS analyzer is a sugar chain showing a mass spectral peak at m/z of 2172 as a result of the mass spectrometry with the MALDI-TOF-MS analyzer. The structural formula is estimated to be: $(Hex)_2(HexNAc)_1(NeuAc)_1+(Man)_3(GlcNAc)_2$ (Table 1).

Moreover, in the present invention, the sugar chain having a peak at the mass-to-charge ratio (m/z) of 2257 in the mass spectrometry conducted using the MALDI-TOF-MS analyzer is a sugar chain showing a mass spectral peak at m/z of 2257 as a result of the mass spectrometry with the MALDI-TOF-MS analyzer. The structural formula is estimated to be: $(Hex)_1(HexNAc)_3(Deoxyhexose)_1+(Man)_3(GlcNAc)_2$ (Table 1).

Moreover, in the present invention, the sugar chain having a peak at the mass-to-charge ratio (m/z) of 2334 in the mass spectrometry conducted using the MALDI-TOF-MS analyzer is a sugar chain showing a mass spectral peak at m/z of 2334 as a result of the mass spectrometry with the MALDI-TOF-MS analyzer. The structural formula is estimated to be: $(Hex)_3(HeXNAc)_1(NeuAc)_1+(Man)_3(GlcNAc)_2$ (Table 1).

Moreover, in the present invention, the sugar chain having a peak at the mass-to-charge ratio (m/z) of 2375 in the mass spectrometry conducted using the MALDI-TOF-MS analyzer is a sugar chain showing a mass spectral peak at m/z of 2375 as a result of the mass spectrometry with the MALDI-TOF-MS analyzer. The structural formula is estimated to be: $(Hex)_2(HexNAc)_2(NeuAc)_1+(Man)_3(GlcNAc)_2$ (Table 1).

Moreover, in the present invention, the sugar chain having a peak at the mass-to-charge ratio (m/z) of 2639 in the mass spectrometry conducted using the MALDI-TOF-MS analyzer is a sugar chain showing a mass spectral peak at m/z of 2639 as a result of the mass spectrometry with the MALDI-TOF-MS analyzer. The structural formula is estimated to be: $(Hex)_3(HexNAc)_4+(Man)_3(GlcNAc)_2$ (Table 1).

Moreover, in the present invention, the sugar chain having a peak at the mass-to-charge ratio (m/z) of 2703 in the mass spectrometry conducted using the MALDI-TOF-MS analyzer is a sugar chain showing a mass spectral peak at m/z of 2703 as a result of the mass spectrometry with the MALDI-TOF-MS analyzer. The structure is estimated to be a Na adduct of the above-described sugar chain showing a mass spectral peak at m/z of 2681 (Table 1).

Moreover, in the present invention, the sugar chain having a peak at the mass-to-charge ratio (m/z) of 2725 in the mass spectrometry conducted using the MALDI-TOF-MS analyzer is a sugar chain showing a mass spectral peak at m/z of 2725 as a result of the mass spectrometry with the MALDI-TOF-MS analyzer. The structural formula is estimated to be: $(Hex)_2(HexNAc)_3(Deoxyhexose)_1(NeuAc)_1+(Man)_3(GlcNAc)_2$ (Table 1).

Moreover, in the present invention, the sugar chain having a peak at the mass-to-charge ratio (m/z) of 2827 in the mass spectrometry conducted using the MALDI-TOF-MS analyzer is a sugar chain showing a mass spectral peak at m/z of 2827 as a result of the mass spectrometry with the MALDI-TOF-MS analyzer. The structural formula is estimated to be: $(Hex)_2(HexNAc)_2(Deoxyhexose)_1(NeuAc)_2+(Man)_3(GlcNAc)_2$ (Table 1).

Moreover, in the present invention, the sugar chain having a peak at the mass-to-charge ratio (m/z) of 3030 in the mass spectrometry conducted using the MALDI-TOF-MS analyzer is a sugar chain showing a mass spectral peak at m/z of 3030 as a result of the mass spectrometry with the MALDI-TOF-MS analyzer. The structural formula is estimated to be: $(Hex)_2(HexNAc)_3(Deoxyhexose)_1(NeuAc)_2+(Man)_3(GlcNAc)_2$ (Table 1).

Thus, the present invention also provides a method for inspecting a gastroenterological cancer, comprising the steps of:
releasing sugar chains from a glycoprotein in blood collected from a subject (step (a));
purifying the released sugar chains (step (b)); and
detecting at least any one of the sugar chains of the above-described structural formulas in the purified sugar chains (step (c)).

In the present invention, an analyzer other than the MALDI-TOF-MS analyzer can also be used, as long as the above-described sugar chains can be detected. As the ion source, it is possible to employ, for example, electron ionization, chemical ionization, field desorption, fast atom bombardment, electrospray ionization, atmospheric-pressure chemical ionization, or the like. In addition, as the analysis method, it is possible to employ a method utilizing, for example, magnetic deflection, quadrupole, ion trap, Fourier transform ion cyclotron resonance, or the like. Moreover, in the present invention, as long as the above-described sugar chains can be detected, high-performance liquid chromatography can be employed, and the above mass spectrometry and high-performance liquid chromatography may be employed in combination.

If necessary, the result of detecting the sugar chain in step (c) is compared with a control value (for example, a detected value from a healthy subject, a detected value from a cancer patient). The present Examples have revealed that, in pancreatic cancer patients, esophageal cancer patients, and stomach cancer patients, a detected value of a sugar chain showing a peak at the mass-to-charge ratio (m/z) of any one of 2521, 2216, and 2054 when the mass spectrometry is conducted with the MALDI-TOF-MS analyzer is significantly lower than a detected value of healthy subjects. Accordingly, if detected values of these sugar chains in a subject are significantly lower than the detected values of the healthy subjects or approximate to the detected values of these cancer patients, it is determined that the subject is suspected of these cancers. Meanwhile, the present Examples have revealed that, in the pancreatic cancer patients and the esophageal cancer patients, a detected value of a sugar chain showing a peak at the mass-to-charge ratio (m/z) of any one of 2681, 3108, and 2695 when the mass spectrometry is conducted with the MALDI-TOF-MS analyzer was significantly higher than a detected value of the healthy subjects. Accordingly, if detected values of these sugar chains in a subject are significantly higher than the detected values of the healthy subjects or approximate to the detected values of these cancer patients, it is determined that the subject is suspected of these cancers. It is also possible to increase the accuracy of inspecting a cancer in the present invention, when the cancer inspection is carried out by combining the results of detecting multiple sugar chains among the above-described sugar chains. Further, by combining the method for inspecting a cancer in the present invention with another already-known method for inspecting a cancer, the accuracy of inspecting a cancer can also be increased.

EXAMPLES

Hereinafter, the present invention will be described more specifically based on Examples and Comparative Example. However, the present invention is not limited to the following Examples.

Example 1

(1) Collecting Blood

Blood was collected from each of patients including pancreatic cancer patients, 34 esophageal cancer patients, and 22 stomach cancer patients as well as 11 healthy subjects as a control, who had given the informed consents. The plasma was centrifuged. The obtained specimen (plasma)) was linkably anonymized, and then frozen at $-80°$ C. for storage.

(2) Preparation of Blood Samples

In order to release proteins and modified sugar chains, the plasma was treated with N-glycosidase F and trypsin. Specifically, to 100 μL of the plasma, pure water (165 μL), 1 M ammonium bicarbonate (25 μL), and 120 mM dithiothreitol (25 μL) were added and left standing at 60° C. for 30 minutes. Then, 123 mM iodoacetamide (50 μL) was added and left standing at room temperature in the dark for 1 hour. Subsequently, trypsin (2000 units, 25 μL) was added and left standing at 37° C. for 1 hour, followed by heating at 80° C. for 15 minutes to denature trypsin. After cooling to room temperature, N-glycosidase F (10 units, 10 μL) was added and left standing at 37° C. overnight. By heating at 80° C. for 15 minutes, the enzyme was denatured, and an enzyme-treated plasma sample in the final amount of 400 μL was obtained. Meanwhile, an internal standard glucose oligomer (1-20) (Seikagaku Corporation, #800111) was dissolved in pure water to be 10 mg/mL, and an internal standard sugar chain solution was prepared. To 95 μL of the enzyme-treated plasma sample, 5 μL (=50 μg equivalent) of the internal standard sugar chain solution was added, and a solution with a total volume of 100 μL was prepared. Of this, 20 μL was treated with sugar chain-capturing beads (BlotGlyco (registered trademark) for MALDI (manufactured by Sumitomo Bakelite Co., Ltd.)), and the released sugar chains were captured and labeled.

(3) Analysis of Sugar Chain-Analysis Result

After purification and separation, the sugar chains captured on the beads were mixed with a matrix (2,5-dihydroxybenzoic acid) solution, and subjected to MALDI-TOF-MS measurement. As the mass spectrometer, Autoflex III smartbeam TOF/TOF (manufactured by Bruker Daltonics Inc.) was used. Moreover, for the data collection and analysis, software appended to the instrument (For example, flexControl, flex-Analysis) were used. Further, the laser ionization was performed in the normal positive ion mode, and the detection was performed in the reflector mode.

From the obtained mass spectrum, 20 to 100 peaks were identified. Of these, 6 kinds of sugar chains, excluding the internal standard sugar chain and the like, were targeted for the analysis for each of pancreatic cancer, stomach cancer, and pancreatic cancer. Each of the sugar chains was quantified in comparison with the internal standard. A total signal amount indicating the abundance of the sugar chains was calculated, and corrected by the percentages of the respective sugar chains.

Figure 2:
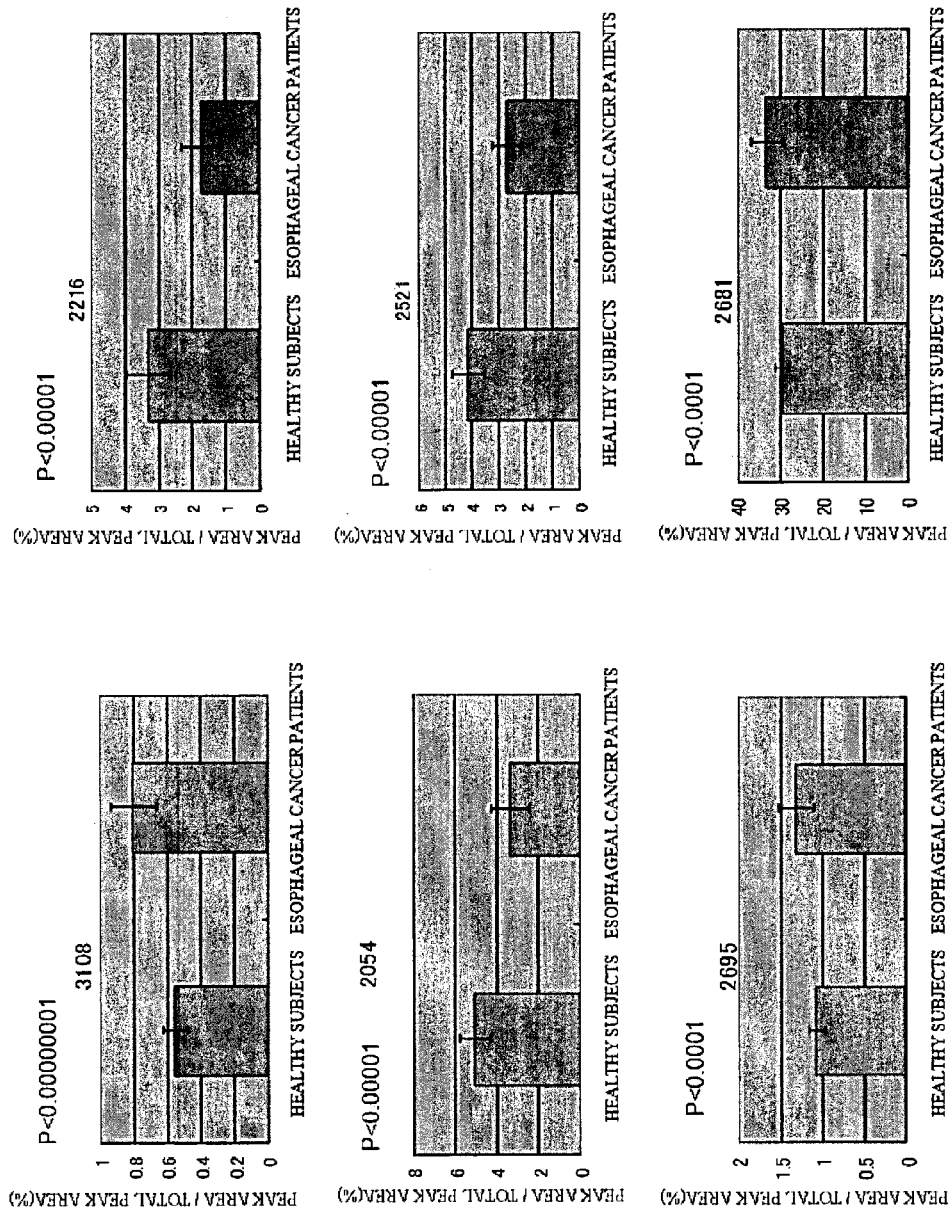
FIG. 2 shows graphs illustrating the result of quantifying the abundance of sugar chains in each specimen, the sugar chains having been determined to be significantly different by a t-test conducted between two groups of the healthy subject group and an esophageal cancer group. A total signal amount indicating the abundance of the sugar chains was calculated, and corrected by the percentages of the sugar chains in the specimen.
Figure 3:
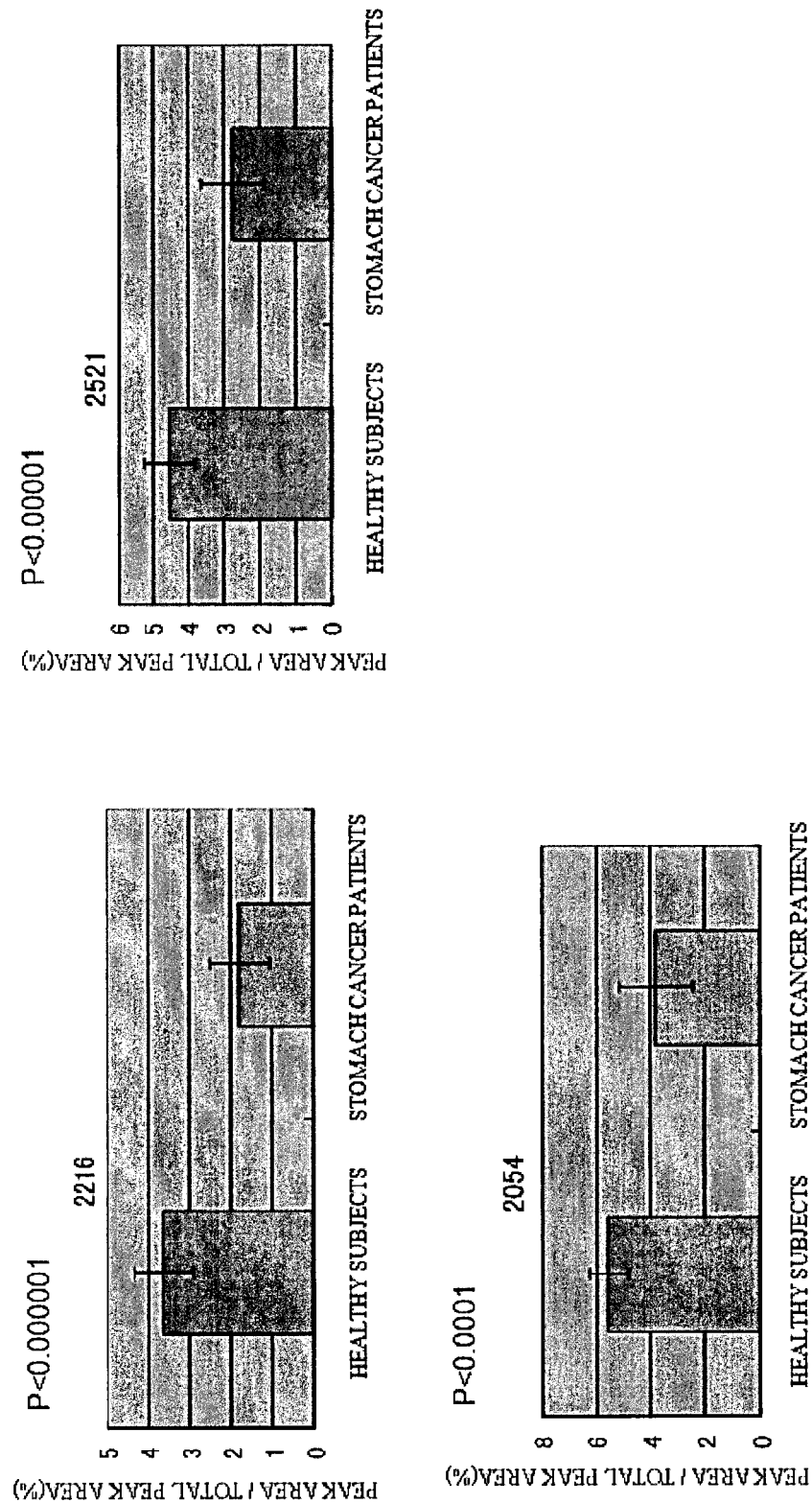
FIG. 3 shows graphs illustrating the result of quantifying the abundance of sugar chains in each specimen, the sugar chains having been determined to be significant difference by a T-test conducted between groups of the healthy subject group and a stomach cancer group. A total signal amount indicating the abundance of the sugar chains was calculated, and corrected by the percentages of the sugar chains in the specimen.

Furthermore, a T-test was conducted between two groups of: the healthy subject group and the pancreatic cancer group; the healthy subject group and the esophageal cancer group; and the healthy subject group and the stomach cancer group. It was attempted to identify sugar chains showing a significant difference between the groups. As a result, as to pancreatic cancer and esophageal cancer, identified were sugar chains showing the mass-to-charge ratio (m/z) of 2521, 2216, 2054, 2681, 3108, and 2695, respectively. As to stomach cancer, identified were sugar chains showing the mass-to-charge ratio (m/z) of 2521, 2216, and 2054, respectively (FIGS. 1 to 3). Note that the peak area/total peak area (%) of the sugar chain showing the mass-to-charge ratio (m/z) of 2521, 2216, or 2054 was significantly low in the cancer patients. The peak area/total peak area (%) of the sugar chain showing 2681, 3108, or 2695 was significantly high in the cancer patients.

Additionally, accuracy ratios using the sugar chain with m/z of 2521 and the sugar chain with m/z of 2216 were calculated using six classiers (Compound Covariate Predictor, Diagonal Linear Discriminant Analysis, 1-Nearest Neighbor Predictor, 3-Nearest Neighbor Predictor, Nearest Centroid Predictor, Support Vector Machine Predictor). As a result, the accuracy ratio of approximately 88% on average was obtained for pancreatic cancer.

Moreover, the structural formulas of the sugar chains were predicted from the signals obtained as the result of the mass spectrometry. Consequently, the structure of the sugar chain showing the mass-to-charge ratio (m/z) of 2521 was predicted to be:

[Chem. 13]

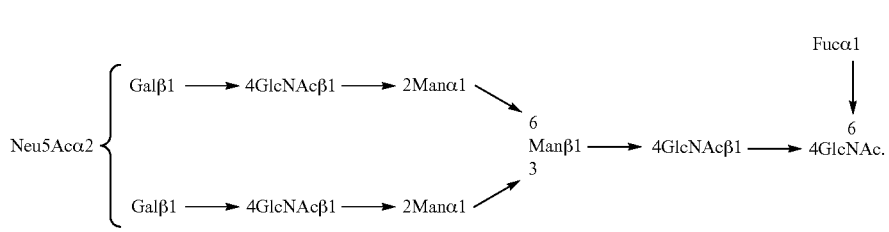

The structure of the sugar chain showing the mass-to-charge ratio (m/z) of 2216 was predicted to be:

[Chem. 14]

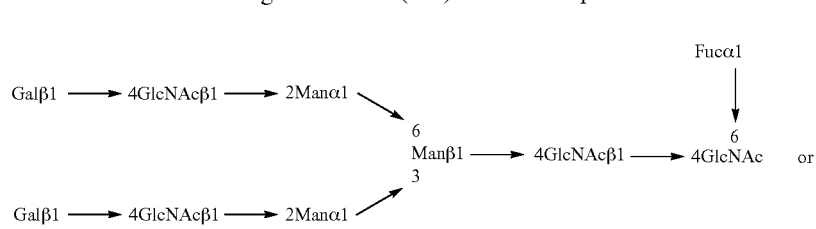

[Chem. 15]

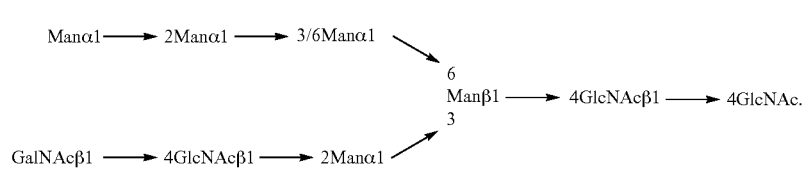

The structure of the sugar chain showing the mass-to-charge ratio (m/z) of 2054 was predicted to be:

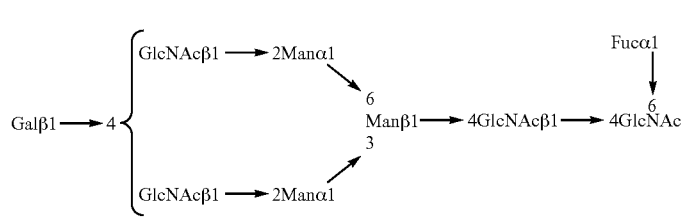

[Chem. 16]

The structure of the sugar chain showing the mass-to-charge ratio (m/z) of 2680 was predicted to be:

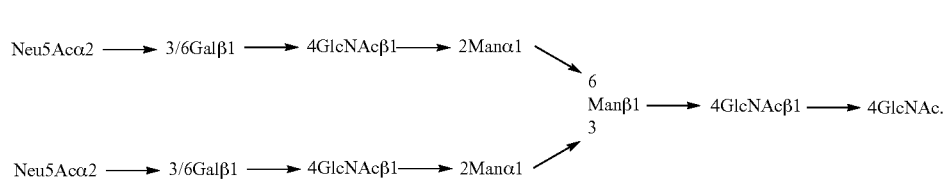

[Chem. 17]

The structure of the sugar chain showing the mass-to-charge ratio (m/z) of 3108 was predicted to be:

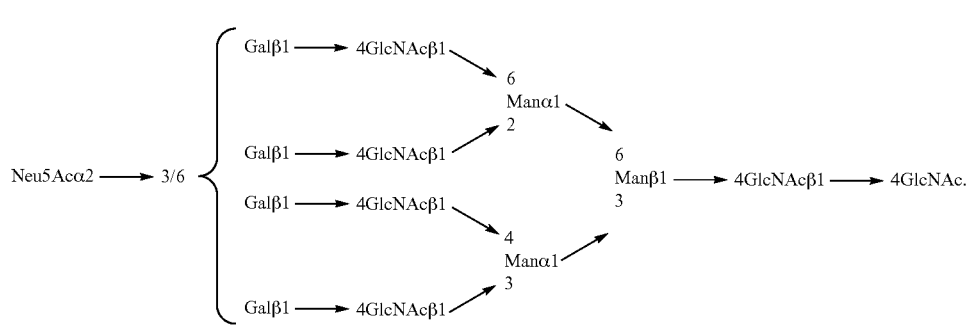

[Chem. 18]

Example 2

(1) Collecting Blood

Blood was collected from each of 17 pancreatic cancer patients and 11 healthy subjects as a control, who had given the informed consents. The plasma was centrifuged. The obtained specimen (plasma) was linkably anonymized, and then frozen at $-80°$ C. for storage.

(2) Preparation of Blood Samples

In order to release proteins and modified sugar chains, the plasma was treated with N-glycosidase F and trypsin. Specifically, to 100 μL of the plasma, pure water (165 μL), 1 M ammonium bicarbonate (25 μL), and 120 mM dithiothreitol (25 μL) were added and left standing at 60° C. for 30 minutes. Then, 123 mM iodoacetamide (50 μL) was added and left standing at room temperature in the dark for 1 hour. Subsequently, trypsin (2000 units, 25 μL) was added and left standing at 37° C. for 1 hour, followed by heating at 80° C. for 15 minutes to denature trypsin. After cooling to room temperature, N-glycosidase F (10 units, 10 μL) was added and left standing at 37° C. overnight. By heating at 80° C. for 15 minutes, the enzyme was denatured, and an enzyme-treated plasma sample in the final amount of 400 μL was obtained.

Meanwhile, an internal standard glucose oligomer (1-20) (Seikagaku Corporation #800111) was dissolved in pure water to be 10 mg/mL, and an internal standard sugar chain solution was prepared. To 95 μL of the enzyme-treated plasma sample, 5 μL (=50 μg equivalent) of the internal standard sugar chain solution was added, and a solution with a total volume of 100 μl was prepared. Of this, 20 μL was treated with sugar chain-capturing beads (BlotGlyco (registered trademark) for MALDI (manufactured by Sumitomo Bakelite Co., Ltd.)), and the released sugar chains were captured and labeled.

(3) Analysis of Sugar Chain-Analysis Result

After purification and separation, the sugar chains captured on the beads were mixed with a matrix (2,5-dihydroxybenzoic acid) solution, and subjected to MALDI-TOF-MS measurement. As the mass spectrometer, Autoflex III smartbeam TOF/TOF (manufactured by Bruker Daltonics Inc.) was used. Moreover, for the data collection and analysis, software appended to the instrument (for example, flexControl, flexAnalysis) were used. Further, the laser ionization was performed in the normal positive ion mode, and detection was performed in the reflector mode.

From the obtained mass spectrum, 20 to 100 peaks were identified. The peaks common among the pancreatic cancer patients were collected. The areas of the peaks of the pancreatic cancer patients and the healthy subjects were analyzed using multivariate analysis software SIMCA-P/P+(manufactured by UMETRICS) to determine peak combinations enabling the two groups (patient group, healthy subject group) to be separated from each other.

Figure 4:
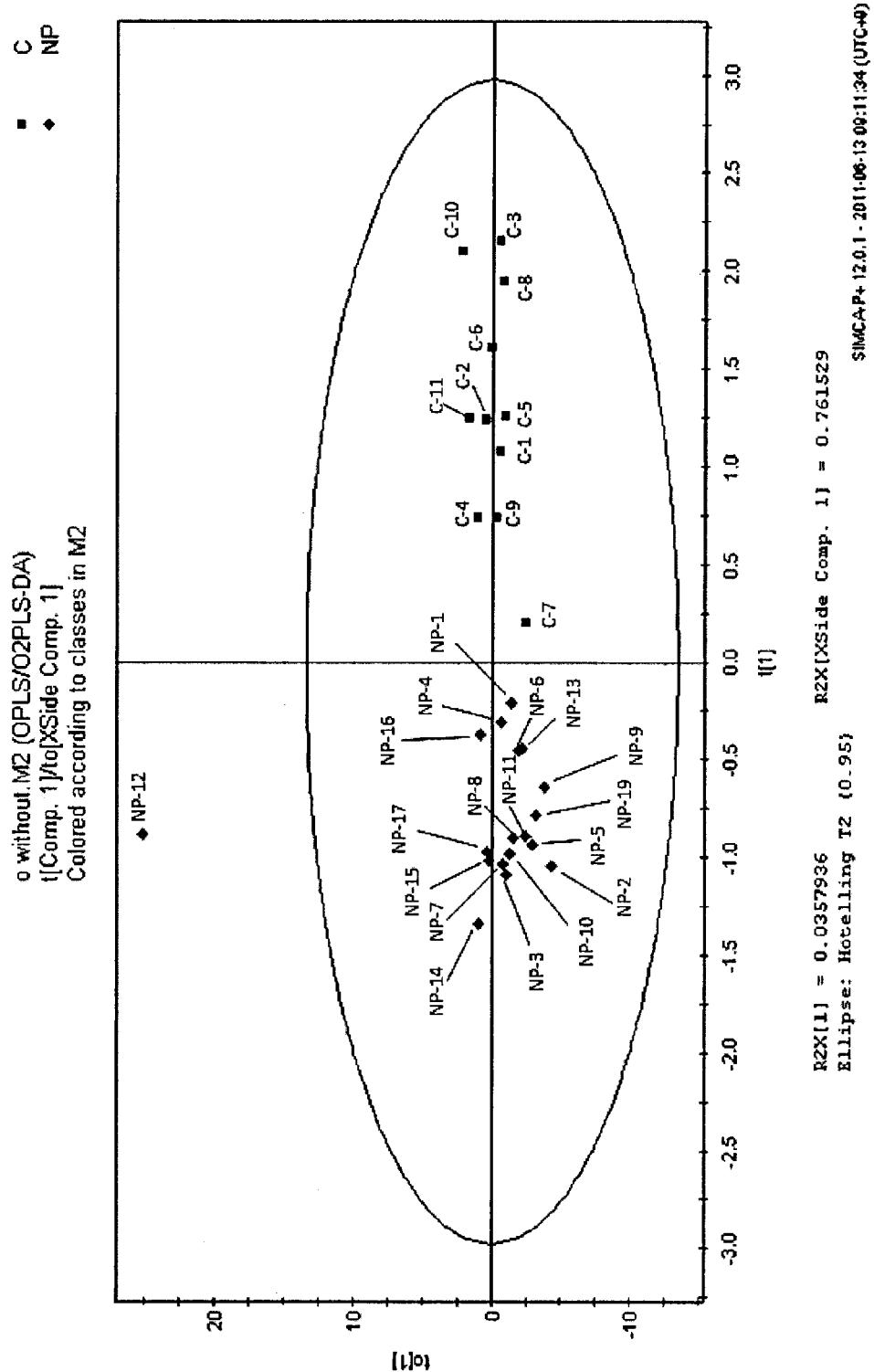
FIG. 4 is a graph showing the result of multivariate analysis on the areas of peaks of pancreatic cancer patients and healthy subjects obtained as the result of mass spectrometry to identify peak combinations that enable two groups (patient group, healthy subject group) to be separated from each other.

As a result, sugar chains having the peaks for separating the two groups from each other were detected. The sugar chains showed the mass-to-charge ratio (m/z) of 1326, 1892, 2054, 2172, 2216, 2257, 2334, 2375, 2521, 2639, 2681, 2703, 2725, 2827, 3030, and 3108 (FIG. 4, Table 1).

TABLE 1

| m/z | δmass | Estimated sugar structure |
|---|---|---|
| 1326 | 1.974 | $(Hex)_2(HexNAc)_2(Deoxyhexose)_1$ |
| 1892 | 0.013 | $(HexNAc)_2(Deoxyhexose)_1 + (Man)_3(GlcNAc)_2$ |
| 2054 | 0.013 | $(Hex)_1(HexNAc)_2(Deoxyhexose)_1 + (Man)_3(GlcNAc)_2$ |
| 2172 | 0.008 | $(Hex)_2(HexNAc)_1(NeuAc)_1 + (Man)_3(GlcNAc)_2$ |
| 2216 | 0.012 | $(Hex)_2(HexNAc)_2(Deoxyhexose)_1 + (Man)_3(GlcNAc)_2$ |
| 2257 | 0.013 | $(Hex)_1(HexNAc)_3(Deoxyhexose)_1 + (Man)_3(GlcNAc)_2$ |
| 2334 | 0.009 | $(Hex)_3(HexNAc)_1(NeuAc)_1 + (Man)_3(GlcNAc)_2$ |
| 2375 | 0.009 | $(Hex)_2(HexNAc)_2(NeuAc)_1 + (Man)_3(GlcNAc)_2$ |
| 2521 | 0.008 | $(Hex)_2(HexNAc)_2(Deoxyhexose)_1(NeuAc)_1 + (Man)_3(GlcNAc)_2$ |
| 2639 | 0.013 | $(Hex)_3(HexNAc)_4 + (Man)_3(GlcNAc)_2$ |
| 2681 | 0.005 | $(Hex)_2(HexNAc)_2(NeuAc)_2 + (Man)_3(GlcNAc)_2$ |
| 2703 | | Na adduct of 2681 |
| 2725 | 0.009 | $(Hex)_2(HexNAc)_3(Deoxyhexose)_1(NeuAc)_1 + (Man)_3(GlcNAc)_2$ |
| 2827 | 0.004 | $(Hex)_2(HexNAc)_2(Deoxyhexose)_1(NeuAc)_2 + (Man)_3(GlcNAc)_2$ |
| 3030 | 0.004 | $(Hex)_2(HexNAc)_3(Deoxyhexose)_1(NeuAc)_2 + (Man)_3(GlcNAc)_2$ |
| 3108 | 2.689 | $(Hex)_4(HexNAc)_4(NeuAc)_1 + (Man)_3(GlcNAc)_2$ |

Note that the symbols in Table 1 mean the followings.
δmass = [measured m/z] − [theoretical m/z]
+: the structure shown on the right side of "+" is a basic structure, and the structure shown on the left side is an additional structure.
Hex: hexose (mannose)
HexNAc: N-acetylhexosamine (N-acetylglucosamine)
Deoxyhexose: fucose
Man: mannose
GlcNAc: N-acetylglycosamine
NeuAc: N-acetylneuraminic acid

INDUSTRIAL APPLICABILITY

The present invention makes it possible to easily inspect a gastroenterological cancer at an early stage of the cancer by detecting a specific N-linked sugar chain in blood collected from a subject. Accordingly, the present invention is useful particularly in the medical field.

The invention claimed is:

1. A method for diagnosing a gastroenterological cancer, comprising:

treating blood collected from a subject such that sugar chains are released from a glycoprotein included in the blood;

purifying the sugar chains released from the glycoprotein such that purified sugar chains are obtained;

detecting at least one sugar chain which indicates presence of gastroenterological cancer in the purified sugar chains; and diagnosing the gastroenterological cancer in the subject based on an amount of the at least one sugar chain detected in the purified sugar chains, wherein the detecting comprises detecting an N-linked sugar chain which shows a peak at a mass-to-charge ratio of one of 2521, 2216, 2054, 2681, 3108, and 2695 when mass spectrometry is conducted with a MALDI-TOF-MS analyzer in a positive ion mode using a matrix solution comprising 2,5-dihydroxybenzoic acid.

2. A method for diagnosing a gastroenterological cancer, comprising:

treating blood collected from a subject such that sugar chains are released from a glycoprotein included in the blood;

purifying the sugar chains released from the glycoprotein such that purified sugar chains are obtained;

detecting in the purified sugar chains at least one sugar chain which indicates presence of gastroenterological cancer and is selected from the group consisting of

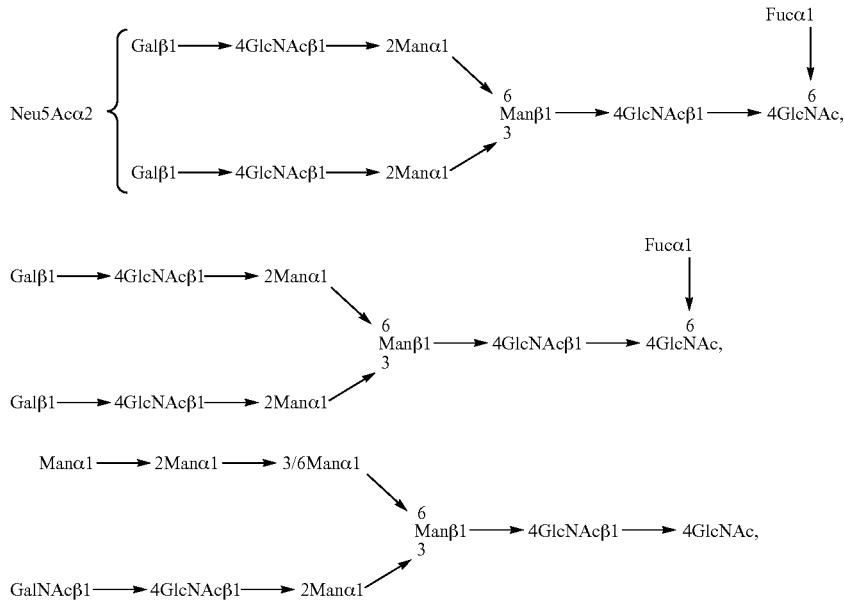

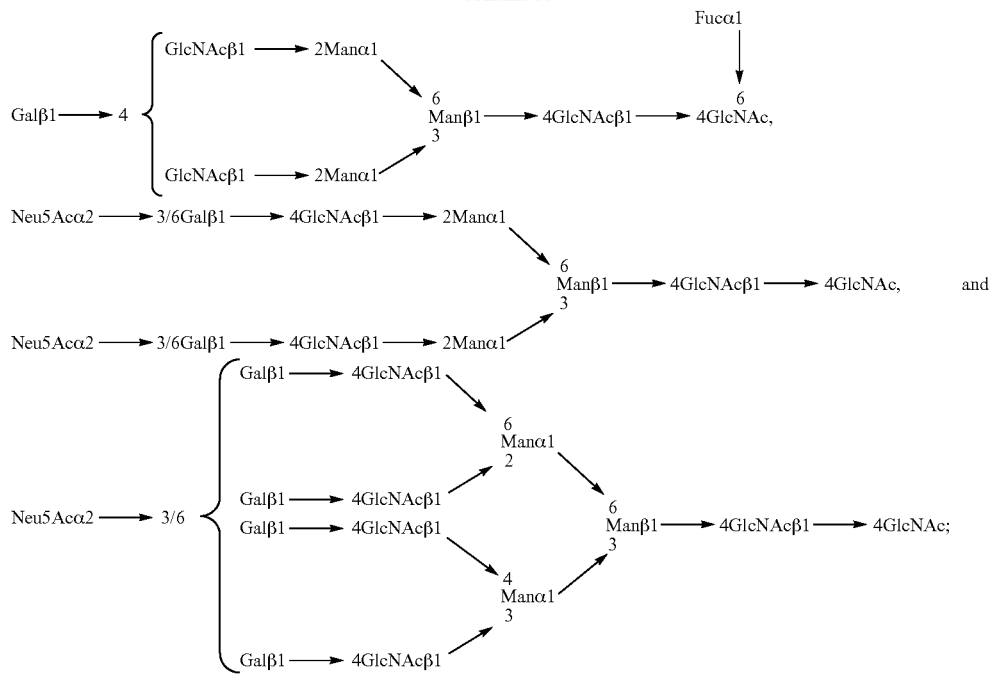

and
diagnosing the gastroenterological cancer in the subject based on an amount of the at least one sugar chain detected in the purified sugar chains,
wherein the detecting comprises performing a MALDI-TOF-MS analysis on the purified sugar chains.

3. The method according to claim 1, wherein the gastroenterological cancer is one of pancreatic cancer, esophageal cancer, and stomach cancer.

4. The method according to claim 1, wherein the sugar chain is an N-linked sugar chain which shows a peak at a mass-to-charge ratio of one of 2521 and 2216.

5. The method according to claim 1, wherein the treating comprises treating the sugar chains by an enzymatic method using N-glycosidase F.

6. The method according to claim 1, wherein the treating comprises treating the sugar chains by an enzymatic method using glycopeptidase A.

7. The method according to claim 1, wherein the treating comprises treating the sugar chains by a hydrazine decomposition method.

8. The method according to claim 1, wherein the treating comprises treating the sugar chains by an enzymatic method using N-glycosidase F in combination with a protease.

9. The method according to claim 1, wherein the treating comprises treating the sugar chains by an enzymatic method using N-glycosidase F in combination with trypsin.

10. The method according to claim 1, wherein the purifying of the sugar chains includes selectively capturing the sugar chains with sugar chain-capturing beads optimized for measurement by MALDI-TOF-MS.

11. The method according to claim 2, wherein the gastroenterological cancer is one of pancreatic cancer, esophageal cancer, and stomach cancer.

12. The method according to claim 2, wherein the sugar chain is at least one sugar chain selected from the group consisting of

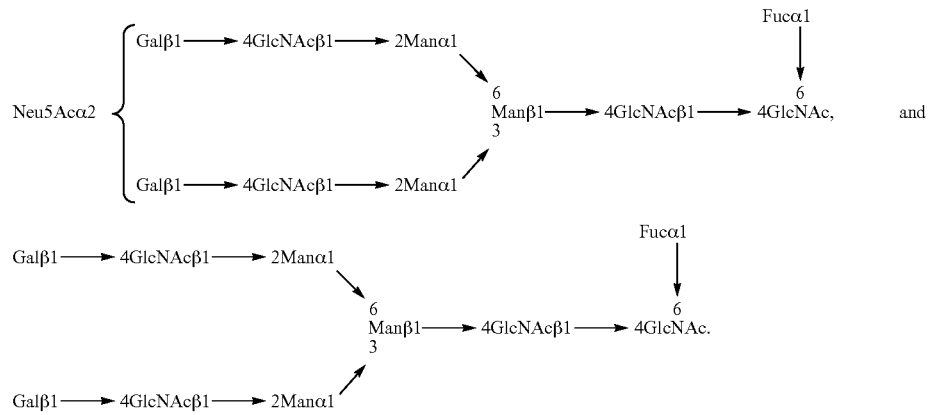

13. The method according to claim 2, wherein the treating comprises treating the sugar chains by an enzymatic method using N-glycosidase F.

14. The method according to claim 2, wherein the treating comprises treating the sugar chains by an enzymatic method using glycopeptidase A.

15. The method according to claim 2, wherein the treating comprises treating the sugar chains by a hydrazine decomposition method.

16. The method according to claim 2, wherein the treating comprises treating the sugar chains by an enzymatic method using N-glycosidase F in combination with a protease.

17. The method according to claim 2, wherein the treating comprises treating the sugar chains by an enzymatic method using N-glycosidase F in combination with trypsin.

18. The method according to claim 2, wherein the purifying of the sugar chains includes selectively capturing the sugar chains with sugar chain-capturing beads optimized for measurement by MALDI-TOF-MS.

19. The method according to claim 12, wherein the gastroenterological cancer is stomach cancer, and the diagnosing comprising diagnosing the subject as having stomach cancer if the at least one sugar chain is detected in a smaller amount than in a subject without stomach cancer.

20. The method according to claim 2, wherein the gastroenterological cancer is esophageal cancer, the sugar chain is at least one sugar chain selected from the group consisting of

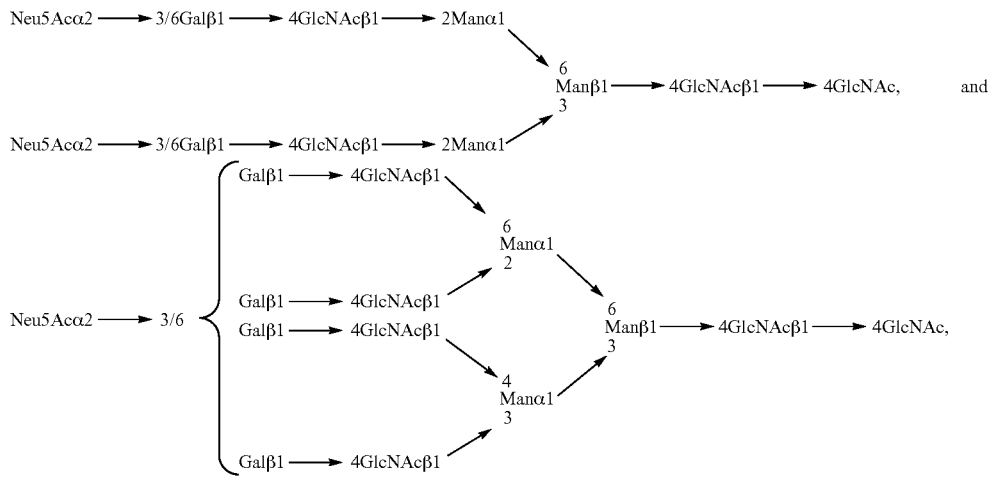

and the diagnosing comprising diagnosing the subject as having esophageal cancer if the at least one sugar chain is detected in a greater amount than in a subject without esophageal cancer.

* * * * *